(12) United States Patent
    Bhattacharya

(10) Patent No.: US 12,614,609 B2
(45) Date of Patent: Apr. 28, 2026

(54) SYSTEMS AND METHODS TO IDENTIFY MUTATIONS IN MITOCHONDRIAL GENOMES

(71) Applicant: Quest Diagnostics Investments LLC, Secaucus, NJ (US)

(72) Inventor: Anindya Bhattacharya, San Juan Capistrano, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 1070 days.

(21) Appl. No.: 17/613,805

(22) PCT Filed: May 26, 2020

(86) PCT No.: PCT/US2020/034578
    § 371 (c)(1),
    (2) Date: Nov. 23, 2021

(87) PCT Pub. No.: WO2020/243108
    PCT Pub. Date: Dec. 3, 2020

(65) Prior Publication Data
    US 2022/0215901 A1    Jul. 7, 2022

Related U.S. Application Data

(60) Provisional application No. 62/853,271, filed on May 28, 2019.

(51) Int. Cl.
    *G16B 20/20*    (2019.01)
    *C12Q 1/6869*    (2018.01)

(52) U.S. Cl.
    CPC ........... *G16B 20/20* (2019.02); *C12Q 1/6869* (2013.01)

(58) Field of Classification Search
    CPC ....... G16B 20/20; G16B 30/10; C12Q 1/6869
    See application file for complete search history.

(56) References Cited

U.S. PATENT DOCUMENTS

| | | | |
|---|---|---|---|
| 9,177,099 B2 | 11/2015 | Ganeshalingam et al. | |
| 2012/0089339 A1* | 4/2012 | Ganeshalingam | ...... G06F 16/22 |
| | | | 702/19 |
| 2015/0094212 A1 | 4/2015 | Gottimukkala et al. | |
| 2018/0057871 A1* | 3/2018 | Weng | ................... C12Q 1/6869 |

OTHER PUBLICATIONS

NCBI, "The Statistics of Sequence Similarity Score", retrieved from https://www.ncbi.nlm.nih.gov/BLAST/tutorial/Altschul-1.html on Aug. 20, 2025, 13 pages.*

Goudenege David et al: "eKLIPse: a sensitive tool for the detection and quantification of mitochondrial DNA deletions from next-generation sequencing data", Genetics in Medicine, Nature Publishing Group US, New York, vol. 21, No. 6, Nov. 5, 2018 (Nov. 5, 2018), pp. 1407-1416, XP036796397, ISSN: 1098-3600, DOT: 10.1038/S41436-018-0350-8 [retrieved on Nov. 5, 2018] * whole document, especially pp. 1407-1409, fig. 1 *.

Supplementary European Search Report dated Jun. 12, 2023 in EP 20813178.

Bosworth, et al., "Detection and quantification of mitochondrial DNA deletions from next-generation sequence data", BMC Bioinformatics 2017, 18 (Suppl 12):407; DOI 10.1186/s12859-017-1821-7.

International Search Report and Written Opinion dated Oct. 5, 2020 in PCT PCT/US2020/034578.

* cited by examiner

*Primary Examiner* — Robert H Havlin
(74) *Attorney, Agent, or Firm* — Duane Morris LLP

(57) ABSTRACT

The present disclosure describes a sequencing system configured to identify structural variants in mitochondrial DNA. Variant callers configured to identify variants in linear genomes (e.g., those found in chromosomes) can fail to properly identify structural variants in mitochondrial DNA. The system and methods can identify structural variants in next generation sequencing data collected from circular, mitochondrial DNA.

17 Claims, 7 Drawing Sheets

Specification includes a Sequence Listing.

100

SEQUENCING SYSTEM
102

NGS SEQUENCER
124

INTERFACE
104

PROCESSOR
106

MEMORY
108

DATA PARSER
110

MAPPING ENGINE
116

FILTERING ENGINE
118

DATA FILE
112

114

REPORTING ENGINE
122

ANALYTICS ENGINE
120

300

1
CTGAGGTGTGTGCTCTGCCTGCAGGCAGCAGAGAAACAAATGAAGGACA
A 51 52                                                      89
AGATGTCGGGGGCGGCGGGCAGGGCTGGCAGGGGGGCAAGGCC

302

6                                                          43
GTCCT[GATGTCGGGGGCGGGGGCAGGGCTGGGGGCAGGGCCAGGAC

95
GAGGAGCAGAGGCTTAAGGAGGAAGAAGACAAGAAACGCAAGACTG

145
ACGTGTGTGCTCTGCCTGCAGGCAGCAGAGAAACAAATGAAGGACAAA]A
A

304

Blat result

|      | R_s | R_e | M_s | M_e |
|------|-----|-----|-----|-----|
| row1 | 1   | 51  | 95  | 145 |
| row2 | 52  | 89  | 6   | 43  |

SEQUENCE LISTING

```
<160> NUMBER OF SEQ ID NOS: 9

<210> SEQ ID NO 1
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gggggcgggc agggctggca gggggtgcag gcagcagaga aacaaatgaa ggac              54

<210> SEQ ID NO 2
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcgggggcgg gcagggctgg caggggggcaa ggccctgagg tgtgtgctct gcctgcaggc      60
agcagagaaa caaatgaagg acaaaca                                           87

<210> SEQ ID NO 3
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gggcagggct ggcaggggggg cagatgcccg gatgcaggca gcagagaaac aaaagagaaa      60
ct                                                                      62

<210> SEQ ID NO 4
<211> LENGTH: 76
<212> TYPE: DNA
<213> ORGANISM: Artificial Sequence
```

<220> FEATURE:
<223> OTHER INFORMATION: Description of Artificial Sequence: Synthetic
     oligonucleotide

<400> SEQUENCE: 4
atgtcggggg cgggcagggc tggcagggggg gcagtgcagg cagcagagaa acaaaagaga        60
aactgaagga caaaca                                                          76

<210> SEQ ID NO 5
<211> LENGTH: 89
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 5
ctgaggtgtg tgctctgcct gcaggcagca gagaaacaaa tgaaggacaa agatgtcggg        60
ggcgggcagg gctggcaggg ggcaaggcc                                          89

<210> SEQ ID NO 6
<211> LENGTH: 147
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 6
gtcctgatgt cgggggcggg cagggctggc aggggggcaag gccaggacga ggagcagagg        60
cttaaggagg aggaagaaga caagaaacgc aagactgagg tgtgtgctct gcctgcaggc       120
agcagagaaa caaatgaagg acaaaaa                                           147

<210> SEQ ID NO 7
<211> LENGTH: 76
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 7
gatgtcgggg gcgggcaggg ctggcagggg gcaaggaacc aggaagtaaa caaagagacg        60
acggacgtcc gtctcg                                                        76

<210> SEQ ID NO 8
<211> LENGTH: 76
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 8
gctctgcctg caggcagcag agaaacaaat gaaggaccaa ggaacggggg acggtcggga        60
cgggcggggg ctgtag                                                        76

<210> SEQ ID NO 9
<211> LENGTH: 148
<212> TYPE: DNA
<213> ORGANISM: Artificial Sequence
<220> FEATURE:
<223> OTHER INFORMATION: Description of Artificial Sequence: Synthetic -continued

```
     polynucleotide

<400> SEQUENCE: 9
gtcctgatgt cgggggcggg cagggctggc aggggggcaag gccaggacga ggagcagagg          60
cttaaggagg aggaagaaga caagaaacgc aagactgagg tgtgtgctct gcctgcaggc         120
agcagagaaa caaatgaagg accaaagg                                            148
```

SYSTEMS AND METHODS TO IDENTIFY MUTATIONS IN MITOCHONDRIAL GENOMES

CROSS-REFERENCE TO RELATED APPLICATION

This application is the U.S. National Stage of PCT/US2020/034578, filed May 26, which claims priority to and benefit of U.S. Provisional Patent Application No. 62/853,271 filed on May 28, 2019, the content of which is incorporated herein by reference in its entirety.

The instant application contains a Sequence Listing which has been submitted in ASCII format via EFS-WEB and is hereby incorporated by reference in its entirety. Said ASCII copy, created on Nov. 23, 2021, is named sequence.txt and is 3,206 bytes.

BACKGROUND OF THE DISCLOSURE

Next-generation sequencing (NGS) can produce large quantities of sequencing data of variable quality. An NGS system can fragment a genome into a plurality of small segments. The segments can be sequenced in parallel and then recombined to generate a complete sequence. Sequence metrics can be calculated on the sequencing data.

SUMMARY OF THE DISCLOSURE

The present disclosure describes systems and methods for identifying structural variants in mitochondrial DNA. Mitochondrial DNA is a short (e.g., 16,569 bases long) circular DNA. The mitochondrial DNA can include structural variants. The structural variant calling methods developed to identity variants in non-mitochondrial DNA can result in improper alignments of the short reads found in the mitochondrial DNA. The variant callers can result in improper alignments because the variant callers are designed to operate on large and linear structures of chromosomal DNA. These variant callers for chromosomal DNA can fail to identify mitochondrial DNA structural variants when applied to mitochondrial DNA. The system and methods described herein can identify variants, such as deletions, insertions, duplications, and inversions, in mitochondrial DNA.

According to at least one aspect of the disclosure, a method to identify variants in mitochondrial sequencing data can include receiving a plurality of sequence reads comprising an indication of sequenced DNA samples. The method can include identifying a subset of the plurality of sequence reads. Each of the subsets of the plurality of sequence reads can partially map to a target mitochondrial DNA sample. The method can include generating a plurality of query sequences based on each of the subsets of the plurality of sequence reads that are partially mapped to the target mitochondrial DNA sample. The method can include calculating a score for each of the subsets of the plurality of sequence reads based on an alignment of the plurality of query sequences with the target mitochondrial DNA sample. The method can include selecting a plurality of test reads. The plurality of test reads can include the subset of the plurality of sequence reads having a score below a predetermined threshold. The method can include identifying a breakpoint for each of the plurality of test reads. The method can include determining a count of the plurality of test reads having the breakpoint at a predetermined location. The method can include identifying a sequence variant based on the count of the plurality of test reads having the breakpoint at the predetermined location.

In some implementations, the DNA samples are pair-end sequenced. The sequence variant is one of a deletion, insertion, duplication, or inversion. The method can include generating a plurality of sequence words from the plurality of query sequences. The method can include aligning each of the plurality of sequence words from the plurality of query sequences to the target mitochondrial DNA sample.

In some implementations, the score is an e-value indicating a probability of the alignment of each of the plurality of query sequences occurring by chance. The method can include identifying the breakpoint for one of the plurality of test reads by determining a distance between a first sequence in one of the plurality of test reads and a second sequence in one of the plurality of test reads is one nucleotide, and determining that a length of a deletion between a first location of the first sequence in the target mitochondrial DNA and a second location of the second sequence in the target mitochondrial DNA is greater than one nucleotide.

In some implementations, identifying the breakpoint for one of the plurality of test reads can include determining a distance between a first location of a first sequence in the target mitochondrial DNA and a second location of a second sequence in the target mitochondrial DNA is one nucleotide, and determining a length of an insertion between the first sequence in one of the plurality of test reads and the second sequence in one of the plurality of test reads. In some implementations, identifying the breakpoint for one of the plurality of test reads can include determining a distance between a first sequence in one of the plurality of test reads and a second sequence in one of the plurality of test reads is one nucleotide, and determining that a length of a duplication between an end location of the first sequence in the target mitochondrial DNA and a start location of the second sequence in the target mitochondrial DNA is greater than one nucleotide. In some implementations, the method can include identifying the breakpoint for one of the plurality of test reads by determining that a location of a sequence in one of the plurality of test reads overlaps with a location of an inverted sequence in one of the plurality of test reads, and determining that a location of the sequence in the target mitochondrial DNA does not overlap with a location of the inverted sequence in the target mitochondrial DNA.

According to at least one aspect of the disclosure, a system to identify variants in mitochondrial sequencing data can include one or more processors to receive a plurality of sequence reads that can include an indication of sequenced DNA samples. The system can identify a subset of the plurality of sequence reads. Each of the subsets of the plurality of sequence reads can partially map to a target mitochondrial DNA sample. The system can generate a plurality of query sequences based on each of the subsets of the plurality of sequence reads that are partially mapped to the target mitochondrial DNA sample. The system can calculate a score for each of the subsets of the plurality of sequence reads based on an alignment of the plurality of query sequences within the target mitochondrial DNA sample. The system can select a plurality of test reads. The plurality of test reads can include the subset of the plurality of sequence reads having a score below a predetermined threshold. The system can identify a breakpoint for each of the plurality of test reads. The system can determine a count of the plurality of test reads having the breakpoint at a predetermined location. The system can identify a sequence variant based on the count of the plurality of test reads having the breakpoint at the predetermined location.

In some implementations, the DNA samples are pair-end sequenced. The sequence variant can be one of a deletion, insertion, duplication, or inversion. The system can generate a plurality of sequence words from the plurality of query sequences. The system can align each of the plurality of sequence words from the plurality of query sequences to the target mitochondrial DNA sample. The score can be an e-value indicating a probability of the alignment of each plurality of query sequences occurring by chance.

The system can determine a breakpoint by determining a distance between a first sequence in one of the plurality of test reads and a second sequence in one of the plurality of test reads is one nucleotide, and determine that a length of a deletion between a first location of the first sequence in the target mitochondrial DNA and a second location of the second sequence in the target mitochondrial DNA is greater than one nucleotide. The system can determine a breakpoint by determining a distance between a first location of a first sequence in the target mitochondrial DNA and a second location of a second sequence in the target mitochondrial DNA is one, and determining a length of an insertion between the first sequence in one of the plurality of test reads and the second sequence in one of the plurality of test reads. In some implementations, the system can determine a break-point by determining a distance between a first sequence in one of the plurality of test reads and a second sequence in one of the plurality of test reads is one nucleotide, and determining that a length of a duplication between an end location of the first sequence in the target mitochondrial DNA and a start location of the second sequence in the target mitochondrial DNA is greater than one nucleotide. In some implementations, the system can determine that a location of a sequence in one of the plurality of test reads overlaps with a location of an inverted sequence in one of the plurality of test reads, and determining that a location of the sequence in the target mitochondrial DNA does not overlap with a location of the inverted sequence in the target mitochondrial DNA.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings:

FIG. 3 discloses SEQ ID NOS 1-2, respectively, in order of appearance. FIG. 4 discloses SEQ ID NOS 3-4, respectively, in order of appearance. FIG. 5 discloses SEQ ID NOS 5-6, respectively, in order of appearance. FIG. 6 discloses SEQ ID NOS 7-9, respectively, in order of appearance.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure describes a sequencing system configured to identify structural variants in mitochondrial DNA. Variant callers configured to identify variants in linear genomes (e.g., those found in chromosomes) can fail to properly identify structural variants in mitochondrial DNA. The variant callers can fail to identify structural variants for a number of reasons. For example, mitochondrial DNA is circular and has a different structure when compared to linear genomes. Second, structural variants can be more common in mitochondrial DNA because cells can include multiple copies of the mitochondrial DNA per cell as opposed to the two copies of the genomes found in nuclear chromosomes. Additionally, mutations occur much more frequently in mitochondrial DNA, and the repair mechanism for mitochondrial DNA is poorer when compared to the repair mechanism for the genomes of nuclear chromosomes. The different structure of mitochondrial DNA and the presence of a significantly higher rate of mutations can inhibit variant callers designed for linear genomes from detecting structural variants in mitochondrial DNA.

Figure 1:
FIG. 1 illustrates a block diagram of an example system to identify variants in mitochondrial sequencing data.

FIG. 1 illustrates a block diagram of an example system 100 to identify variants in mitochondrial sequencing data. The system 100 can include a sequencing system 102 and a NGS sequencer 124. The sequencing system 102 can include an interface 104, a processor 106, and memory 108. The memory 108 can include a data parser 110. The memory 108 can include a plurality of data files 112 that are stored in a data repository 114. The memory 108 can include a mapping engine 116 and a filtering engine 118. The memory 108 can include an analytics engine 120 and a reporting engine 122.

The system 100 can include one or more sequencing systems 102. The sequencing system 102 can include at least one server or computer having at least one processor 106. For example, the sequencing system 102 can include a plurality of servers located in at least one data center or server farm or the sequencing system 102 can be a desktop computer. The processor 106 can include a microprocessor, application-specific integrated circuit (ASIC), field-programmable gate array (FPGA), other special purpose logic circuits, or combinations thereof. The sequencing system 102 can be a data processing system as described in relation to FIG. 7. The sequencing system 102 can include a user interface (e.g., a graphical user interface) that is rendered and displayed to the user via a display coupled with the sequencing system 102. One or more input/output (I/O) devices can be coupled with the sequencing system 102.

The sequencing system 102 can include one or more interfaces 104. The sequencing system 102 can receive data from the NGS sequencer 124 via the interface 104. The interface 104 can be a network interface. The sequencing system 102 can receive data from the NGS sequencer 124 via a network. For example, the sequencing system 102 and NGS sequencer 124 can both be components of a local network. In some implementations, the NGS sequencer 124 can transmit the data to a remote server and the sequencing system 102 can download the data from the remove server.

The interface 104 can include any type and form of interface, including Ethernet including 10 Base T, 100 Base T, or 1000 Base T ("Gigabit"); any of the varieties of 802.11 wireless, such as 802.11a, 802.11b, 802.11g, 802.11n, or 802.11ac; cellular, including CDMA, LTE, 3G, or 4G cellular; Bluetooth or other short range wireless connections; or any combination of these or other interfaces.

The interface 104 can be an input/output (I/O) interface. For example, the interface 104 can be any electronic device that conveys data to a user by generating sensory information (e.g., a visualization on a display, one or more sounds, tactile feedback, etc.) and/or converts received sensory information from a user into electronic signals (e.g., a keyboard, a mouse, a pointing device, a touch screen display, a microphone, etc.). The interface 104 can be built-in display or a display external to the sequencing system 102. The interface 104 can include a port or connection. For example, the interface 104 can be a USB port, Firewire, Thunderbolt, or other port for receiving and transmitting data.

The sequencing system 102 can include a data parser 110. The data parser 110 can be any script, file, program, application, set of instructions, or computer-executable code, that is configured to enable the sequencing system 102 to read, write, and manipulate data files 112. The data parser 110 can read the data files 112 from the data repository 114. The data files 112 can include raw data from the NGS sequencer 124. The data files 112 can include a plurality of sequence reads (which can be referred to as "reads") that indicate the sequence of DNA bases in a sample. The data files 112 can be stored as sequence alignment maps (e.g., SAM files). The data files 112 can include text-based data. The data files 112 can be stored in the data repository 114 in a compressed, binary format. For example, the data files 112 can be stored as binary alignment maps (e.g., BAM files). The data parser 110 can decompress the data files 112 before extracting the sequencing data from the data files 112. The data parser 110 can read the data files 112 from the data repository 114, which can be stored on the hard drive of the sequencing system 102.

The data parser 110 can pre-process the data received from the NGS sequencer 124. For example, the data parser 110 can pre-process the raw data received from the NGS sequencer 124 to generate the BAM files (e.g., data files 112). The data parser 110 can pre-process the raw data by mapping the raw data to a reference genome. The reference genome can include human chromosome data including mitochondrial DNA. The data parser 110 can map each read pair in the raw data to the reference genome. The data parser 110 can remove duplicates from the raw data. For example, the data parser 110 can identify read pairs that are likely to have originated from duplicates of the same original DNA fragments. The data parser 110 can recalibrate the base quality scores of the read pairs. The recalibration by the data parser 110 can remove patterns of systematic errors in the base quality scores. The data parser 110 can recalibrate the data by determining covariate statistics from all base calls in the data and adjusting the base quality scores based on the covariate statistics. The data parser 110 can generate a plurality of data files 112 that can be BAM files and can include a plurality of nucleotide sequences. Each of the nucleotide sequences can be referred to as a read. Each of the data files 112 can include a plurality of reads.

The sequencing system 102 can include a mapping engine 116. The mapping engine 116 can be an application, applet, script, service, daemon, routine, or other executable logic to map reads to reference or target genomes. The mapping engine 116 can map the data files 112 (e.g., the data pre-processed by the data parser 110) to mitochondrial DNA. The mapping engine 116 can map the reads in the data files 112 to the mitochondrial DNA. The mapping engine 116 can identify the reads in the data files 112 that map to the mitochondrial DNA. The mapping engine 116 can identify the reads in the data files 112 that do not map or partially map to the mitochondrial DNA. The mapping engine 116 can identify the reads that do not map or partially map to the mitochondrial DNA by setting a flag the read. In some implementations, the mapping engine 116 can sort the reads into different categories or portions. For example, the mapping engine 116 can identify, retrieve, and group all the reads that mapped to the mitochondrial DNA. The mapping engine 116 can identify, retrieve, and group all the reads that did not map or only partially mapped to the mitochondrial DNA into a second subset of the reads. In some implementations, the sequencing system 102 can process the subset of the reads that did not map or only partially mapped to the mitochondrial DNA for variant identification.

The mapping engine 116 can also align reads to a target genome. The target genome can include mitochondrial DNA. For example, the mapping engine 116 can align the reads that were not mapped or only partially mapped to the mitochondrial DNA with the mitochondrial DNA. The mapping engine 116 can include a basic local alignment search tool (BLAST) algorithm to align the reads with a target genome. The mapping engine 116 can include a BLAST-like alignment tool (BLAT) algorithm to align the reads with a target genome. The mapping engine 116 can use the reads that were not mapped or only partially mapped to the mitochondrial DNA as query sequences. The mapping engine 116 can align the query sequences with the mitochondrial DNA by locating short sequence matches within a query sequence and the mitochondrial DNA. For example, the mapping engine 116 can divide each query sequence into a plurality of "words" of a predetermined length. The words can have a sequence length of, for example, three letters (e.g., bases). Neighboring words can have an overlap of length−1. For example, for the query sequence "TCGAGGCA," the mapping engine 116 can divide the query sequence into the words of length 3 to generate the words TCG, CGA, GAC, etc. For each of the query sequences, the mapping engine 116 can calculate a score for the alignment of the query sequence with the mitochondrial DNA. The score can be a function of the number of words generated from the query sequence that aligned with mitochondrial DNA, the number of words generated from the query sequence that did not align with the mitochondrial DNA, and the size of the gap formed by the non-aligning words. In some implementations, the score can be an e-value and can indicate the likelihood that the query sequence could randomly align with the mitochondrial DNA. For example, the lower the e-value, the lower the chance that the query sequence would randomly align with the mitochondrial DNA.

The sequencing system 102 can include a filtering engine 118. The filtering engine 118 can be any script, file, program, application, set of instructions, or computer-executable code, that is configured to enable a computing device on which the filtering engine 118 is executed to select reads from the plurality of query sequences mapped by the mapping engine 116 to the mitochondrial DNA. For example, the filtering engine 118 can load a filtering policy. The filtering policy can include a threshold value for scores (e.g., e-values) calculated by the mapping engine 116. For example, the threshold value can be 1e-30 and the filtering engine 118 can filter out, or otherwise exclude from further processing or analysis, query sequences that do not have a score less than the predetermined threshold value. The filtering engine 118 can exclude from further analysis query sequences that have a score above the predetermined threshold value. In some implementations, query sequences with a score above the predetermined threshold value are more likely to occur by chance when compared to the query sequences with a score below the predetermined threshold. In some implementations, the filtering policy can include a number required of alignments. For example, the filtering policy can indicate a number of alignments required for the filtering engine 118 to pass the read for further processing. In some implementations, the filtering policy can indicate that the read must include at least two non-overlapping portions that align with the mitochondrial DNA. In some implementations, the filtering policy can indicate that the read must include between about 2 and about 10, between about 2 and about 6, or between about 2 and about 4 non-overlapping portions that align with the mitochondrial DNA. The filtering engine 118 can flag the reads that pass the filtering policy (e.g., have a score below the predetermined threshold and have at least two non-overlapping portions that align with the mitochondrial DNA). For example, the filtering engine 118 can set a bit associated with the reads. In some implementations, the filtering engine 118 can write the reads that pass the filtering policy to a buffer or file. The filtering engine 118 can discard or otherwise exclude the reads that do not pass the filtering policy for further processing.

The sequencing system 102 can include an analytics engine 120. The analytics engine 120 can be any script, file, program, application, set of instructions, or computer-executable code, that is configured to enable a computing device on which the analytics engine 120 is executed to calculate sequencing statistics. The analytics engine 120 can calculate the sequencing statistics to identify variants in the mitochondrial DNA. The variants can include deletions, insertions, duplications, and inversions. The calculation of the statistics and the identification of deletions, insertions, duplications, and inversions are further described in relation to FIGS. 2-6, among others. The analytics engine 120 can determine the breakpoints where deletions, insertions, duplications, or inversions occur in the reads. The sequencing statistics can include a calculation of the frequency of each of the variants. The analytics engine 120 can calculate the frequency of each of the variants by counting the number of split reads that are clipped (hard- or soft-clipped) at the breakpoint. The analytics engine 120 can calculate the frequency as the percentage of reads including a breakpoint at the breakpoint location versus the total number of reads. The minimum can be the number of split reads supporting a variant.

The sequencing system 102 can include a reporting engine 122. The reporting engine 122 can be any script, file, program, application, set of instructions, or computer-executable code that is configured to enable a computing device on which the reporting engine 122 is executed to generate reports based on the data generated by the analytics engine 120. The reporting engine 122 can receive the data generated by the analytics engine 120, as the detection and sequencing statistics of a deletion, insertion, duplication, or inversion. The reporting engine 122 can generate reports based on the data.

The sequencing system 102 can include the data repository 114. The data repository 114 can include one or more local or distributed databases. The data repository 114 can include computer data storage or memory and can store one or more data files 112. The data repository 114 can include non-volatile memory such as one or more hard disk drives (HDDs) or other magnetic or optical storage media, one or more solid state drives (SSDs) such as a flash drive or other solid state storage media, one or more hybrid magnetic and solid state drives, one or more virtual storage volumes such as a cloud storage, or a combination thereof.

The sequencing system 102 can store one or more data files 112 in the data repository 114. Each of the data files 112 can include a plurality of gene sequence data, such as sequence reads. The gene sequence data can include an indication of a chromosome, an indication of a position, a base value, and a quality score. The gene sequence data can include mitochondrial DNA sequence data.

The data files 112 can be data files that are in the variant call format (VCF), sequence alignment mapping (SAM) format, binary sequence alignment mapping (BAM), of other file data file formats used in bioinformatics. For example, the data files 112 can include text data or binary data. In some implementations, the data files 112 can include strings of sequencing data. In some implementations, the data files 112 can include sequencing data that identifies the differences between a reference sequence and a sample sequence.

For example, the VCF file format can be used to store sequence variations. The VCF file format can be used to store single nucleotide polymorphisms (SNP), short (e.g., less than 10 base pairs) insertions and deletions, and large structural variants. The VCF file format (and other file formats) can include a header section and a body section. The header section can include metadata that further describes the data within the body of the VCF file format. The body of the VCF file format can include a plurality of columns. Each row can indicate a variation. The columns can identify the chromosome on which the variation is call; a position of the variation in the sequence; an identifier of the variation; a reference base value for the position; an alternative base value for position (e.g., which based other than the reference base was read at the position); a score; and a flag indicating which of a given set of filters the variation passed.

The data parser 110 can include a NGS sequencer 124. The NGS sequencer 124 can generate the data files 112. The system 100 can include a plurality of NGS sequencers 118. The NGS sequencer 124 can be provided samples from which the NGS sequencer 124 generates sequencing data. The NGS sequencer 124 can save the data into one of the above-described file formats. In some implementations, the NGS sequencer 124 can transmit the data files 112 to the sequencing system 102 via a network. In some implementations, the NGS sequencer 124 can transmit the data files 112 to an intermediary device such as cloud-based storage or a removable hard drive. The data files 112 can be transferred from the intermediary device to the sequencing system 102.

Figure 2:
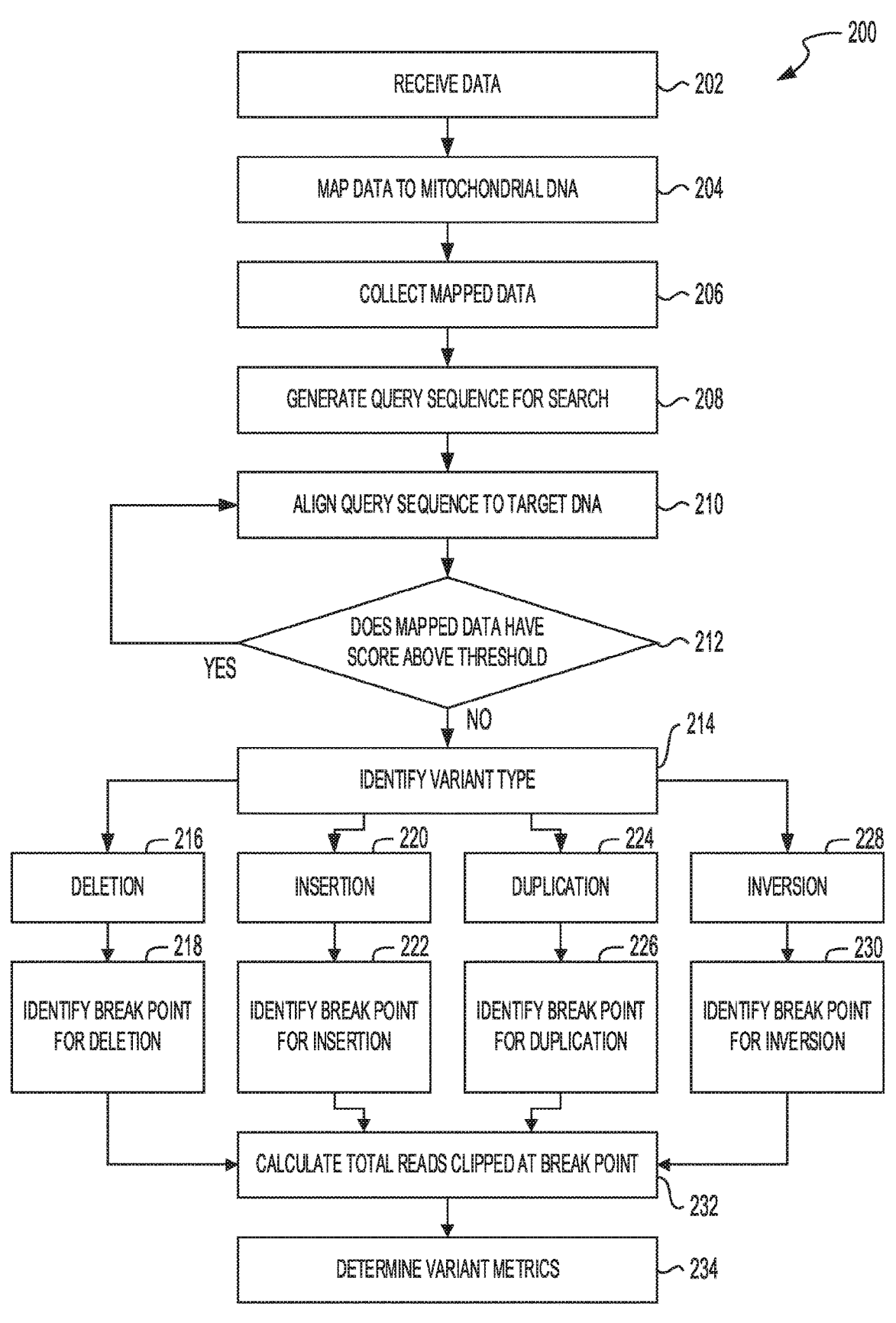
FIG. 2 illustrates a block diagram of an example method to identify variants in mitochondrial sequencing data.

FIG. 2 illustrates a block diagram of an example method 200 to identify variants in mitochondrial sequencing data. The method 200 can include receiving data (BLOCK 202). Also referring to FIG. 1, among others, the sequencing system 102 can receive the sequencing data from the NGS sequencer 124. The analytics engine 120 can receive the sequencing data at the interface 104 from the NGS sequencer 124. The sequencing system 102 can save the sequencing data to data files 112 in the data repository 114. In some implementations, the sequencing system 102 can receive the sequencing data as data files 112 and in some implementations the sequencing system 102 can generate the data files 112 from the raw data received from the NGS sequencer 124. In some implementations, the received data can be DNA data. The DNA data can include mitochondrial DNA samples. In some implementations, the received data can include a non-mitochondrial DNA sample. For example, the data can be a data sample containing less than 50,000, 40,000, 30,000, 20,000, or 10,000 base pairs.

For example, the sequencing system 102 can receive the data as raw data that the data parser 110 can pre-process to generate the data files 112. The data can include pair-end sequencing of DNA samples. The DNA samples can include mitochondrial DNA. The data parser 110 can pre-process the raw data by removing duplicates in the raw data, recalibrating the raw data, and then realigning the raw data, as described above. Receiving the data can include reading the data in the data files 112 into the working memory (e.g., a buffer stored in RAM) of the sequencing system 102. The data can include a plurality of "reads." Each read can include a sequences of DNA bases. Each read can be saved to the data file 112 in a text-based format or a binary-based format.

The method 200 can include mapping the data to mitochondrial DNA (BLOCK 204). The mapping engine 116 can map or align the reads to mitochondrial DNA. The mapping engine 116 can flag the reads as mapping to the mitochondrial DNA, partially mapping to the mitochondrial DNA, or not mapping to the mitochondrial DNA. For example, the mapping engine 116 can set a flag, in a corresponding data file 112 or secondary data file, for each read to indicate whether the read maps, does not map, or partially maps to the mitochondrial DNA. The sequencing system 102 can use a BWA algorithm determine whether the read maps, does not map, or partially maps to the mitochondrial DNA.

The method 200 can include collecting the mapped data (BLOCK 206). The mapping engine 116 can collect the reads that did not map or only partially mapped to the mitochondrial DNA. The sequencing system 102 can identify variants in the mitochondrial DNA. The sequencing system 102 can skip or not further process the reads that mapped to the mitochondrial DNA because the reads to not include variants as the mapped reads aligned with the reference mitochondrial DNA. The reads that did not map or only partially mapped to the reference mitochondrial DNA may include variants, which can account for the reads' inability to map fully to the reference mitochondrial DNA. The mapping engine 116 can collect the reads that did not map or only partially mapped to the mitochondrial DNA into a subset of the samples from the data file 112. For example, the mapping engine 116 can parse through the data files 112 to identify the reads that have a flag indicating the read partially mapped or did not map to the mitochondrial DNA. The mapping engine 116 can write the subset of the reads that did not map or only partially mapped to the mitochondrial DNA to secondary data files 112. The mapping engine 116 can write the subset of the reads that did not map or only partially mapped to the mitochondrial DNA to a buffer of the sequencing system 102.

The method 200 can include generating query sequences (BLOCK 208). The mapping engine 116 can generate query sequences from each of the reads in the subset of reads that did not map or only partially mapped to the mitochondrial DNA. The query sequences can be the reads that did not map or only partially mapped to the mitochondrial DNA. The mapping engine 116 can generate a plurality of query sequences for an inverted version of the reads in the subset of reads that did not map or only partially mapped to the mitochondrial DNA. In some implementations, the mapping engine 116 can use each read as a query sequence and each inverted version of each read as a query sequence. The mapping engine 116 can generate words from each of the query sequences. The words, as described above, can include a length and an overlap.

The method 200 can include aligning the query sequences to target data (BLOCK 210). The mapping engine 116 can map or align the query sequences to the target data. The mapping engine 116 can map the words generated from each of the query sequences to the target data. The target data can be mitochondrial DNA. The mapping engine 116 can map or align the query sequences to the target data with a search algorithm that can align segments or portions of a query sequence (e.g., a word) to target sequences in the target data and allow for gaps between the mapped portions of the target data. For example, the mapping engine 116 can map or align the query sequences to the target data with a BLAT search. The mapping engine 116 can generate a score for the mapping of each of the query sequences to the target data. The score can be an e-value that can indicate the likelihood of the match happening by chance.

The method 200 can include determining whether each query sequence has a score above a threshold (BLOCK 212). The mapping engine 116 can calculate a score for each query sequence. The mapping engine 116 can write the score to a data file. Once the mapping engine 116 calculates the scores, the filtering engine 118 can read or otherwise receive the scores. The filtering engine 118 can retrieve a filtering policy that can include a threshold value. The filtering engine 118 can set the threshold at the threshold value included in the filtering policy. The filtering engine 118 can discard the query sequences that have a score above the threshold value. The filtering engine 118 can discard the query sequences with a score above the threshold value to retain only the query sequences that have a high probability of not occurring by chance.

The method 200 can return to BLOCK 210 to process the next query sequence if the query sequence has a score above the predetermined threshold. If the query sequence's score is below the predetermined threshold, the method 200 can move to BLOCK 214 to determine identify a variant included in the query sequence.

The method 200 can include identifying a variant type in the read (BLOCK 214). The method 200 can include processing through BLOCKS 216 and 218 to identify deletions, through BLOCKS 220 and 222 to identify insertions, through BLOCKS 224 and 226 to identify duplications, and through BLOCKS 228 and 230 to identify inversions. In some implementations, the sequencing system 102 can process through each of the pathways steaming from BLOCK 214 in parallel. For example, the sequencing system 102 can process BLOCKS 216, 220, 224, and 228 in parallel. In some implementations, the sequencing system 102 can process through each of the pathways steaming from BLOCK 214 in series. For example, the sequencing system 102 can process through BLOCKS 216 and 218 and progress to BLOCKS 220 and 222 if the sequencing system 102 does not detect a deletion.

Figure 3:
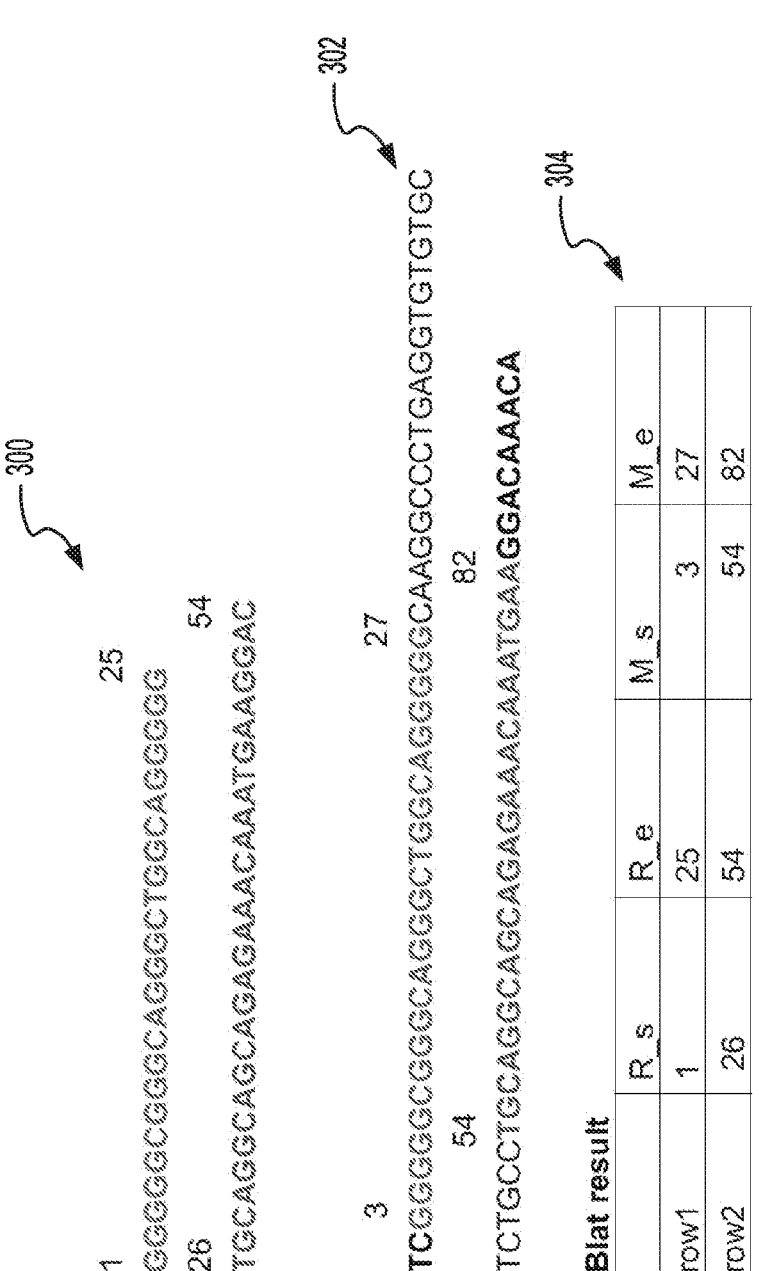
FIGS. 3-6 illustrate examples of identifying variants in mitochondrial sequencing data.

The method 200 can include performing deletion detection (BLOCK 216). Also referring to FIG. 3, FIG. 3 illustrates the mapping of a query sequence 300 to a target sequence 302. FIG. 3 also illustrates a table 304 that includes the BLAT results. The table 304 includes a column (R_s) that indicates the start position of the first row in the query sequence and the start position of the second row in the query sequence. The table 304 include a column (R_e) that indicates the end position of the first row in the query sequence and the end position of the second row in the query sequence. The table 304 includes a column (M_s) that indicates the start position of the query sequence in the target sequence 302 for the first row and the second row. The table 304 includes a column (M_e) that indicates the end position of the query sequence in the target sequence 302 for the first row and the second row. The sequencing system 102 can determine whether the query sequence includes a deletion by determining the distance between the start of second row of the query sequence 300 and the end of the first row the of the query sequence 300. That is, with reference to FIG. 3, the sequencing system 102 can calculate the distance as (row2, R_s)–(row1,R_e). If the distance is 1 (e.g., (row2, R_s)–(row1, R_e)==1), the sequencing system 102 can determine the length of the possible deletion. The length of the deletion can be the number of bases between the position at which the query sequence is located in the target sequence 302. With reference to FIG. 3, the sequencing system 102 can calculate the length of the deletion as (row2, M_s)–(row1, M_e). The sequencing system 102 can determine there is a deletion when the distance between the rows of the query sequence is 1 and the length of the deletion is greater than 1. The method 200 can include determining the breakpoint for the deletion (BLOCK 218). With reference to FIG. 3, the location of the deletion breakpoint can be 5':(row1, M_e)–3':(row2, M_s). For the example illustrated in FIG. 3, the sequencing system 102 can calculate the breakpoint as 5':27–3':54.

Figure 4:
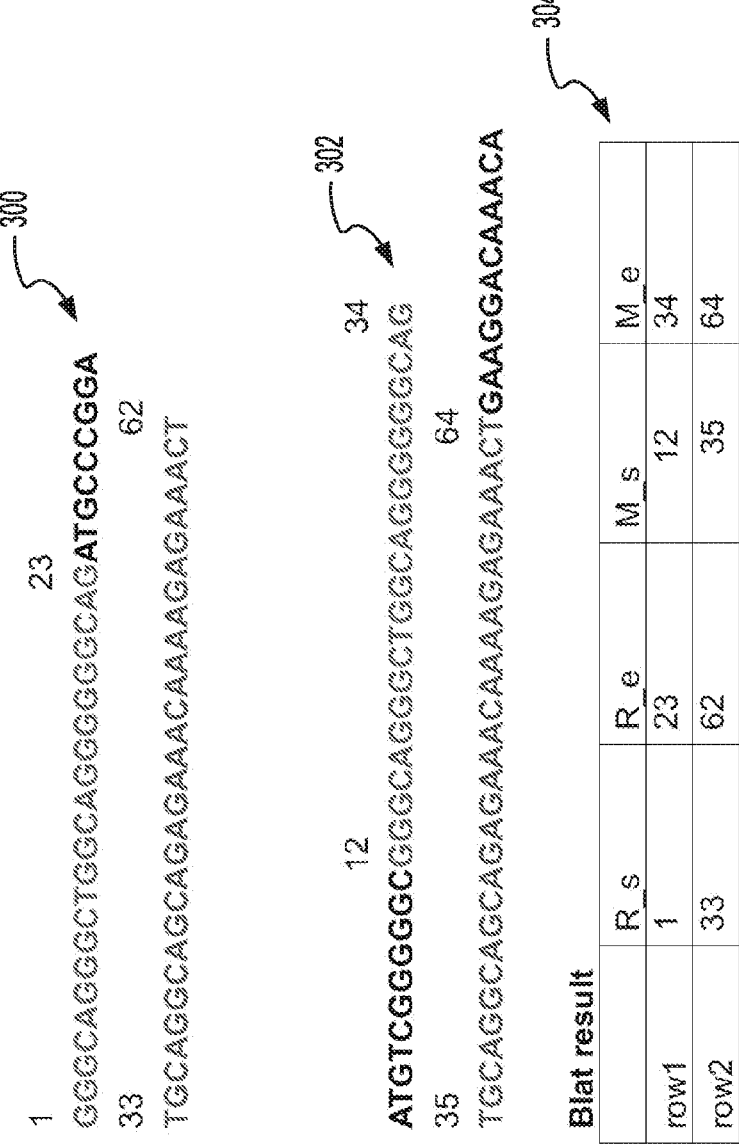

The method 200 can include performing insertion detection (BLOCK 220). Also referring to FIG. 4, FIG. 4 illustrates the mapping of a query sequence 300 to a target sequence 302. FIG. 4 also illustrates a table 304 that includes the BLAT results. The table 304 includes a column (R_s) that indicates the start position of the first row in the query sequence and the start position of the second row in the query sequence. The table 304 include a column (R_e) that indicates the end position of the first row in the query sequence and the end position of the second row in the query sequence. The table 304 includes a column (M_s) that indicates the start position of the query sequence in the target sequence 302 for the first row and the second row. The table 304 includes a column (M_e) that indicates the end position of the query sequence in the target sequence 302 for the first row and the second row.

The sequencing system 102 can determine the query sequence 300 includes an insertion based by determining a length of the possible insertion, the distance between the rows of the target sequence 302, and based on a read sequence length. For example, the sequencing system 102 can determine the there is a possible insertion when the distance between the position of the first row of the query sequence 300 and the second row of the query sequence 300 is greater than one nucleotide. With reference to FIG. 4, sequencing system 102 can determine the length of the possible insertion as (row2, R_s)–(row1, R_e) with the condition that the length be greater than one base long. The sequencing system 102 can determine the distance between the rows of the target sequence 302 as (row 2, M_s)–(row1, M_e). The sequencing system 102 can determine that there is possibly an insertion when the distance between the rows of the target sequence 302 is one nucleotide, e.g., (row 2, M_s)–(row1, M_e)==1. The sequencing system 102 can determine the read sequence length as ((row1, M_e)–(row1, M_s))+((row2, M_e)–(row2, M_s))+(length of insertion). In some implementations, the sequencing system 102 can determine there is an insertion when the length of insertion (e.g., (row2, R_s)–(row1, R_e)) is greater than one nucleotide and the distance between the rows of the target sequence 302 (e.g., (row2, M_s)–(row1, M_e) is one nucleotide. The method 200 can include determining the location of the breakpoint for the insertion. The breakpoint for the insertion can be 5':(row1, M_e)–3':(row2, M_s). For the example illustrated in FIG. 4, the sequencing system 102 can calculate the breakpoint as 5':34–3':35.

Figure 5:
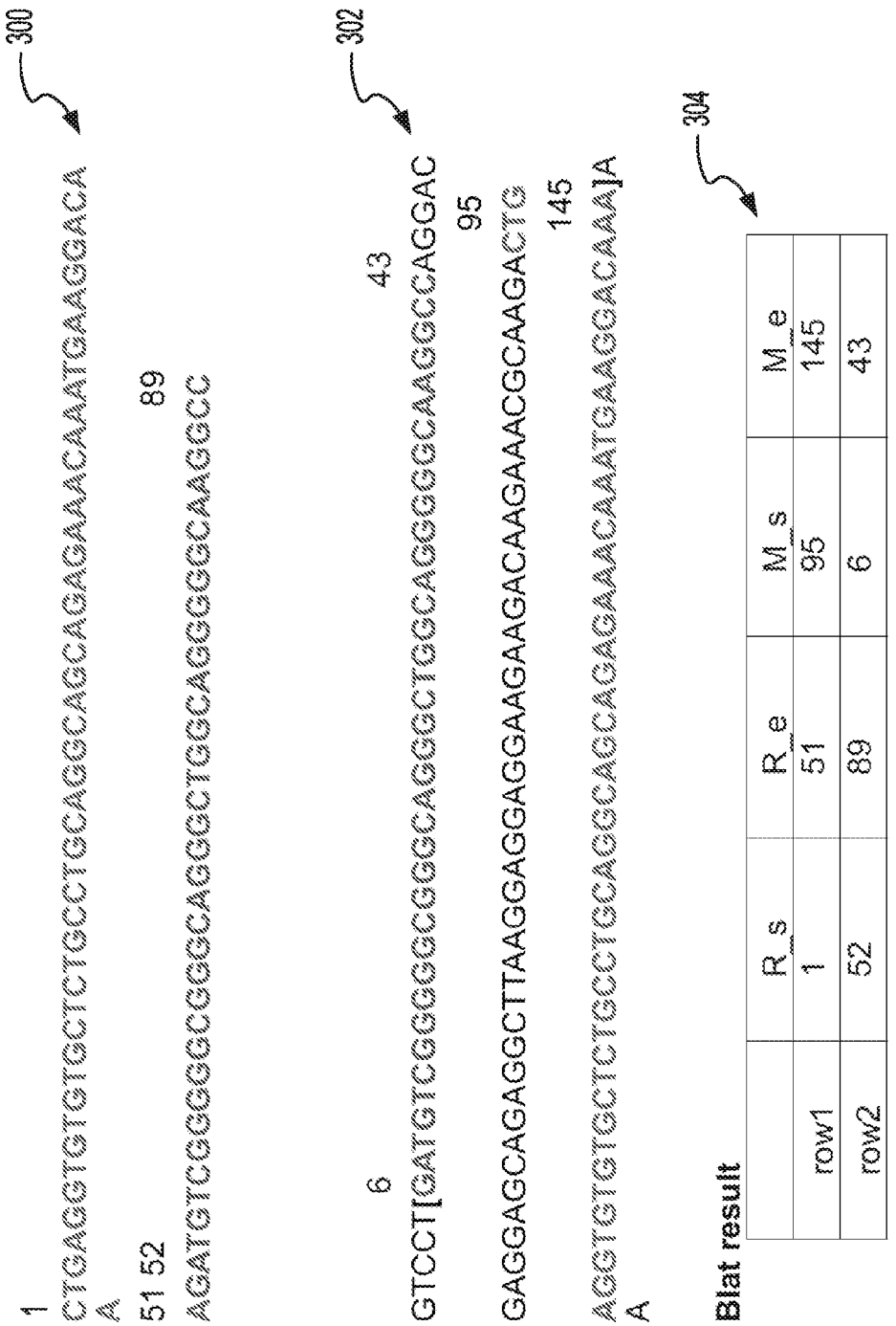

The method 200 can include performing duplication detection (BLOCK 224). Also referring to FIG. 5, FIG. 5 illustrates the mapping of a query sequence 300 to a target sequence 302. FIG. 5 also illustrates a table 304 that includes the BLAT results. The table 304 includes a column (R_s) that indicates the start position of the first row in the query sequence and the start position of the second row in the query sequence. The table 304 include a column (R_e) that indicates the end position of the first row in the query sequence and the end position of the second row in the query sequence. The table 304 includes a column (M_s) that indicates the start position of the query sequence in the target sequence 302 for the first row and the second row. The table 304 includes a column (M_e) that indicates the end position of the query sequence in the target sequence 302 for the first row and the second row.

The sequencing system 102 can determine the query sequence 300 includes a duplication based on the distance between the end of the first row of the query sequence 300 and the start of the second row of the query sequence 300 and based on the length of the possible duplication region. For example, the sequencing system 102 can determine the distance query sequence 300 can include a possible duplication when the distance between the end of the first row of the query sequence 300 and the start of the second row of the query sequence 300 is one nucleotide. For example, and with reference to FIG. 5, the sequencing system 102 can determine the query sequence 300 includes a possible duplication when (row2, R_s)–(row1, R_e)==1. The sequencing system 102 can determine the query sequence 300 includes a possible duplication when the length of the duplication is greater than one. nucleotide For example, and with reference to FIG. 5, the sequencing system 102 can determine the length of the duplication as (row1, M_e)–(row2, M_s). The sequencing system 102 can determine the query sequence 300 includes a duplication when the distance between the end of the first row of the query sequence 300 and the start of the second row of the query sequence 300 is 1 (e.g., (row2, R_s)–(row1, R_e)==1) and when the length of the duplication is greater than 1 (e.g., (row1, M_e)–(row2, M_s)>1. The method 200 can include determine the location of the breakpoint for the duplication (BLOCK 226). The sequencing system 102 can determine the location of the breakpoint as 5':(row2, M_s)–3':(row1, M_e). In the example illustrated in FIG. 5, the location of the breakpoint can be 5':6–3':145.

Figure 6:
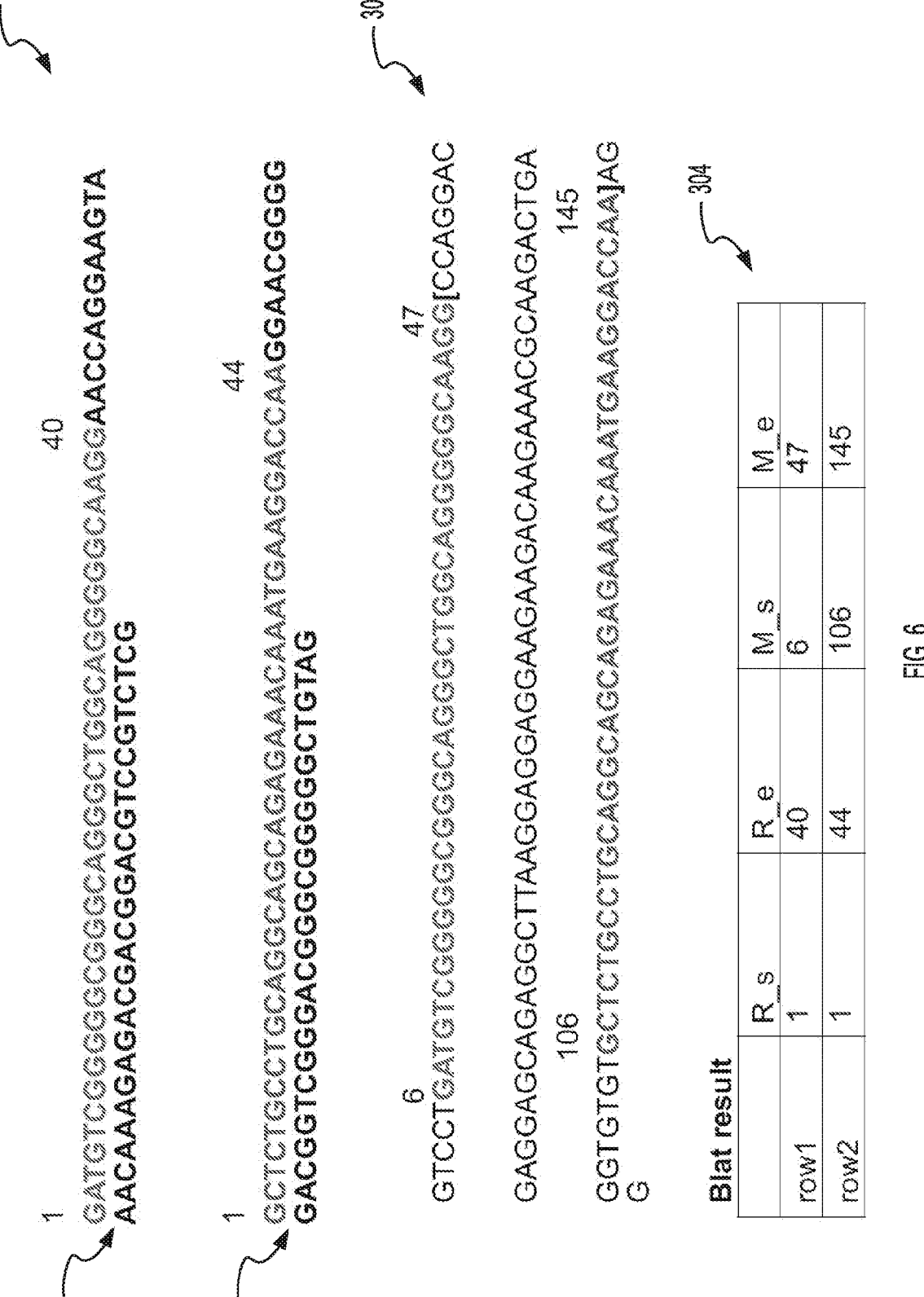

The method 200 can include performing inversion detection (BLOCK 228). Also referring to FIG. 6, FIG. 6 illustrates the mapping of a query sequence 300 to a target sequence 302. The query sequence 300 includes can include a first read 600 and a second read 602. The second read 602 can be an inverted read of the search query. FIG. 6 also illustrates a table 304 that includes the BLAT results. The table 304 includes a column (R_s) that indicates the start position of the first row in the query sequence and the start position of the second row in the query sequence. The table 304 include a column (R_e) that indicates the end position of the first row in the query sequence and the end position of the second row in the query sequence. The table 304 includes a column (M_s) that indicates the start position of the query sequence in the target sequence 302 for the first row and the second row. The table 304 includes a column (M_e) that indicates the end position of the query sequence in the target sequence 302 for the first row and the second row.

The sequencing system 102 can detect inversion in the query sequence 300 when there is overlap of the read sequence in the query sequence 300 and no overlap of the read sequence when mapped to the target sequence 302. For example, and also referring to FIG. 6, the sequencing system 102 can detect inversion when there is no overlap between the sequence defined between (row1, M_s) and (row1, M_e) and the sequence defined between (row2, M_s) and (row2, M_e). The sequencing system 102 can detect inversion when there is overlap between the first read 600 of the query sequence 300 and the second read 602 (e.g., the inverted read) of the query sequence 300. For example, and also referring to FIG. 6, the sequencing system 102 can determine there is an inversion when there is overlap between the sequence defined between (row1, R_s) and (row1, R_e) and the sequence defined between (row2, R_s) and (row2, R_e). In some implementations, the sequencing system 102 can determine there is inversion when there is no overlap between the sequence defined between (row1, M_s) and (row1, M_e) and the sequence defined between (row2, M_s) and (row2, M_e), but there is overlap between the first read 600 of the query sequence 300 and the second read 602 (e.g., the inverted read) of the query sequence 300. The method 200 can include determining the breakpoint location of the inversion (BLOCK 230). The sequencing system 102 can calculate the location of the breakpoint for the inversion as 5':(row1, M_e)–3':(row2, M_e). In the example illustrated in FIG. 6, the breakpoint location can be 5':47–3':145.

The method 200 can include calculating the total reads that are clipped at the breakpoint locations (BLOCK 232). The analytics engine 120 can collect each of the breakpoint locations identified at BLOCKS 218, 222, 226, and 230. The analytics engine 120 can group similar breakpoints. For example, the analytics engine 120 can group each of the breakpoints associated with deletions, each of the breakpoints associated with insertions, etc. The analytics engine 120 can determine the count of the reads that are clipped at each of the breakpoint locations. The analytics engine 120 can determine the count of the reads that are hard or soft clipped at each of the breakpoint locations. In some implementations, the analytics engine 120 can include the number of split reads in each of the counts.

The method 200 can include determining variant metrics (BLOCK 234). The variant metrics can include an event frequency. For example, the analytics engine 120 can, for each of the breakpoint locations, determine a frequency at which the breakpoints occur. For example, for each of the breakpoints locations, the frequency of the breakpoint location can be the percentage as a function of the count of the number of times the breakpoint location occurred to the total number of reads at the breakpoint location.

In some implementations, an identified variant can be validated against known mitochondrial variants. For example, the sequencing system 102 can include a database that includes known mitochondrial variants. The sequencing system 102 can populate the database from public or other databases of known mitochondrial variants. The sequencing system 102 can search the database of known mitochondrial variants to determine whether the identified variant is a true positive or a true negative. In some implementations, the sequencing system 102 can validate the variant based on a weighting determined using the database of known mitochondrial variants. For example, inclusion or exclusion of a variant identified by the sequencing system 102 may not be determinative of whether the variant is a true positive or true negative. In this example, the sequencing system 102 can generate a score for the validity of the variant based on a weighted combination of the determined metrics for the variant (as determined at BLOCK 234, for example) and the inclusion or exclusion of the variant in the database of known variants.

Figure 7:
FIG. 7 illustrates a block diagram of an example computer system.
Figure 7:
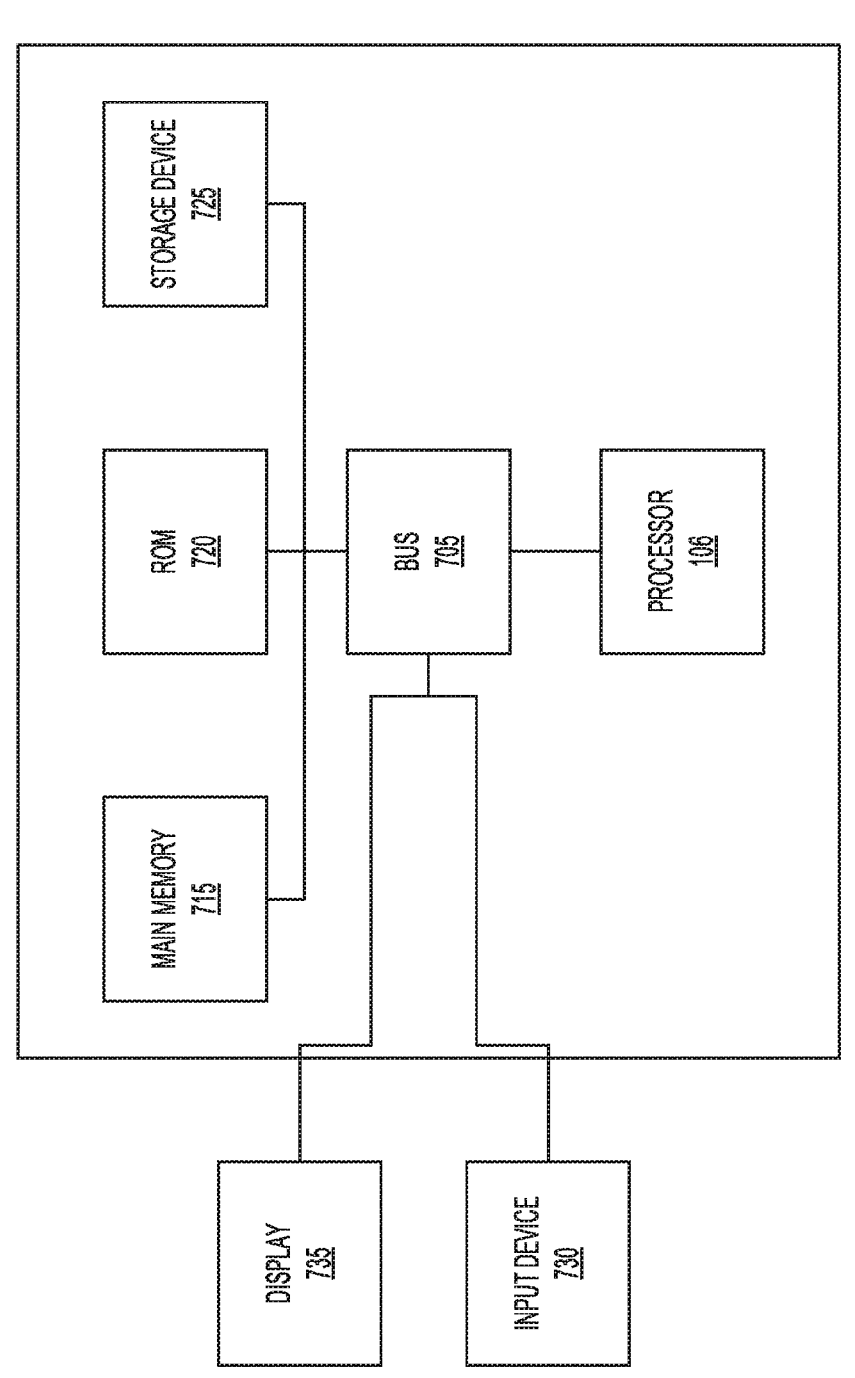

FIG. 7 illustrates a block diagram of an example computer system. The computer system or computing device 700 can include or be used to implement the system 100 or its components such as the sequencing system 102. The computing system 700 includes a bus 705 or other communication component for communicating information and a processor 106 or processing circuit coupled to the bus 705 for processing information. The computing system 700 can also include one or more processors 106 or processing circuits coupled to the bus for processing information. The computing system 700 also includes main memory 715, such as a random access memory (RAM) or other dynamic storage device, coupled to the bus 705 for storing information, and instructions to be executed by the processor 106. The main memory 715 can be or include the data repository 114 and the data files 112. The main memory 715 can be or can include the memory 108. The main memory 715 can also be used for storing position information, temporary variables, or other intermediate information during execution of instructions by the processor 106. The computing system 700 may further include a read only memory (ROM) 720 or other static storage device coupled to the bus 705 for storing static information and instructions for the processor 106. A storage device 725, such as a solid state device, magnetic disk or optical disk, can be coupled to the bus 705 to persistently store information and instructions. The storage device 725 can include or be part of the memory 108.

The computing system 700 may be coupled via the bus 705 to a display 735, such as a liquid crystal display, or active matrix display, for displaying information to a user. An input device 730, such as a keyboard including alphanumeric and other keys, may be coupled to the bus 705 for communicating information and command selections to the processor 106. The input device 730 can include a touch screen display 735. The input device 730 can also include a cursor control, such as a mouse, a trackball, or cursor direction keys, for communicating direction information and command selections to the processor 106 and for controlling cursor movement on the display 735. The display 735 can be part of the sequencing system 102 or other component of FIG. 1, for example.

The processes, systems and methods described herein can be implemented by the computing system 700 in response to the processor 106 executing an arrangement of instructions contained in main memory 715. Such instructions can be read into main memory 715 from another computer-readable medium, such as the storage device 725. Execution of the arrangement of instructions contained in main memory 715 causes the computing system 700 to perform the illustrative processes described herein. One or more processors in a multi-processing arrangement may also be employed to execute the instructions contained in main memory 715. Hard-wired circuitry can be used in place of or in combination with software instructions together with the systems and methods described herein. Systems and methods described herein are not limited to any specific combination of hardware circuitry and software.

Although an example computing system has been described in FIG. 7, the subject matter including the operations described in this specification can be implemented in other types of digital electronic circuitry, or in computer software, firmware, or hardware, including the structures disclosed in this specification and their structural equivalents, or in combinations of one or more of them.

The subject matter and the operations described in this specification can be implemented in digital electronic circuitry, or in computer software, firmware, or hardware, including the structures disclosed in this specification and their structural equivalents, or in combinations of one or more of them. The subject matter described in this specification can be implemented as one or more computer programs, e.g., one or more circuits of computer program instructions, encoded on one or more computer storage media for execution by, or to control the operation of, data processing apparatuses. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. While a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices). The operations described in this specification can be implemented as operations performed by a data processing apparatus on data stored on one or more computer-readable storage devices or received from other sources.

The terms "data processing system" "computing device" "component" or "data processing apparatus" encompass various apparatuses, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures. The components of system 100 can include or share one or more data processing apparatuses, systems, computing devices, or processors.

A computer program (also known as a program, software, software application, app, script, or code) can be written in any form of programming language, including compiled or interpreted languages, declarative or procedural languages, and can be deployed in any form, including as a standalone program or as a module, component, subroutine, object, or other unit suitable for use in a computing environment. A computer program can correspond to a file in a file system. A computer program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs (e.g., components of the sequencing system 102) to perform actions by operating on input data and generating output. The processes and logic flows can also be performed by, and apparatuses can also be implemented as, special purpose logic circuitry, e.g., an FPGA (field programmable gate array) or an ASIC (application specific integrated circuit). Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

---

What is claimed:

1. A method to identify variants in mitochondrial sequencing data, comprising:

receiving a plurality of sequence reads comprising an indication of sequenced DNA samples;

identifying a subset of the plurality of sequence reads, wherein each sequence read of the subset of the plurality of sequence reads is partially mapped or not mapped to a target mitochondrial DNA sample;

generating a plurality of query sequences from the subset of the plurality of sequence reads that are partially mapped to the target mitochondrial DNA sample or inverted versions of the subset of the plurality of sequence reads;

calculating a score for each of the subset of the plurality of sequence reads based on an alignment of the plurality of query sequences with the target mitochondrial DNA sample, wherein the score is an e-value indicating a probability of the alignment of each plurality of query sequences occurring by chance;

selecting a plurality of test reads, wherein the plurality of test reads comprises the subset of the plurality of sequence reads having a score below a predetermined threshold;

identifying a breakpoint for each of the plurality of test reads;

determining a count of the plurality of test reads having the breakpoint at a predetermined location of the target mitochondrial DNA sample;

identifying a sequence variant based on the count of the plurality of test reads having the breakpoint at the predetermined location, wherein the sequence variant is one of a deletion, insertion, duplication, or inversion; and generating a report identifying the sequence variant from the sequenced DNA samples.

2. The method of claim 1, wherein the DNA samples are pair-end sequenced.

3. The method of claim 1, further comprising generating a plurality of sequence words from the plurality of query sequences.

4. The method of claim 3, further comprising aligning each of the plurality of sequence words from the plurality of query sequences to the target mitochondrial DNA sample.

5. The method of claim 1, wherein identifying the breakpoint for one of the plurality of test reads comprises:

determining a distance between a first sequence in the one of the plurality of test reads and a second sequence in one of the plurality of test reads is one nucleotide; and determining that a length of a deletion between a first location of the first sequence in the target mitochondrial DNA sample and a second location of the second sequence in the target mitochondrial DNA sample is greater than one nucleotide.

6. The method of claim 1, wherein identifying the breakpoint for one of the plurality of test reads comprises:

determining a distance between a first location of a first sequence in the target mitochondrial DNA sample and a second location of a second sequence in the target mitochondrial DNA sample is one nucleotide; and determining a length of an insertion between the first sequence in the one of the plurality of test reads and the second sequence in the one of the plurality of test reads.

7. The method of claim 1, wherein identifying the breakpoint for one of the plurality of test reads comprises:

determining a distance between a first sequence in the one of the plurality of test reads and a second sequence in the one of the plurality of test reads is one nucleotide; and determining that a length of a duplication between an end location of the first sequence in the target mitochondrial DNA sample and a start location of the second sequence in the target mitochondrial DNA sample is greater than one nucleotide.

8. The method of claim 1, wherein identifying the breakpoint for one of the plurality of test reads comprises:

determining that a location of a sequence in the one of the plurality of test reads overlaps with a location of an inverted sequence in the one of the plurality of test reads; and determining that a location of the sequence in the target mitochondrial DNA sample does not overlap with a location of the inverted sequence in the target mitochondrial DNA sample.

9. The method of claim 1, further comprising validating the sequence variant against a database comprising known mitochondrial DNA variants.

10. A system to identify variants in mitochondrial sequencing data, comprising one or more processors to:

receive a plurality of sequence reads comprising an indication of sequenced DNA samples;

identify a subset of the plurality of sequence reads, wherein each sequence read of the subset of the plurality of sequence reads is partially mapped to a target mitochondrial DNA sample;

generate a plurality of query sequences from the subset of the plurality of sequence reads that are partially mapped to the target mitochondrial DNA sample or inverted versions of the subset of the plurality of sequence reads;

calculate a score for each of the subset of the plurality of sequence reads based on an alignment of the plurality of query sequences with the target mitochondrial DNA sample;

wherein the score is an e-value indicating a probability of the alignment of each plurality of query sequences occurring by chance;

select a plurality of test reads, wherein the plurality of test reads comprises the subset of the plurality of sequence reads having a score below a predetermined threshold;

identify a breakpoint for each of the plurality of test reads;

determine a count of the plurality of test reads having the breakpoint at a predetermined location of the target mitochondrial DNA sample;

identify a sequence variant based on the count of the plurality of test reads having the breakpoint at the predetermined location, wherein the sequence variant is one of a deletion, insertion, duplication, or inversion; and generate a report identifying the sequence variant from the sequenced DNA samples.

11. The system of claim 10, wherein the DNA samples are pair-end sequenced.

12. The system of claim 10, further comprising the one or more processors to generate a plurality of sequence words from the plurality of query sequences.

13. The system of claim 12, further comprising the one or more processors to align each of the plurality of sequence words from the plurality of query sequences to the target mitochondrial DNA sample.

14. The system of claim 12, further comprising the one or more processors to:

determine a distance between a first sequence in the one of the plurality of test reads and a second sequence in one of the plurality of test reads is one nucleotide;

determine that a length of a deletion between a first location of the first sequence in the target mitochondrial DNA sample and a second location of the second sequence in the target mitochondrial DNA sample is greater than one nucleotide; and calculate the breakpoint for the one of the plurality of test reads based on the distance and the length of the deletion.

15. The system of claim 12, further comprising the one or more processors to:

determine a distance between a first location of a first sequence in the target mitochondrial DNA sample and a second location of a second sequence in the target mitochondrial DNA sample is one nucleotide;

determine a length of an insertion between the first sequence in the one of the plurality of test reads and the second sequence in the one of the plurality of test reads; and calculate the breakpoint for the one of the plurality of test reads based on the distance and the length of the insertion.

16. The system of claim 12, further comprising the one or more processors to:

determine a distance between a first sequence in the one of the plurality of test reads and a second sequence in the one of the plurality of test reads is one nucleotide; and determine that a length of a duplication between an end location of the first sequence in the target mitochondrial DNA sample and a start location of the second sequence in the target mitochondrial DNA sample is greater than one nucleotide; and calculate the breakpoint for the one of the plurality of test reads based on the distance and the length of the duplication.

17. The system of claim 12, further comprising the one or more processors to:

determine that a location of a sequence in the one of the plurality of test reads overlaps with a location of an inverted sequence in the one of the plurality of test reads; and determine that a location of the sequence in the target mitochondrial DNA sample does not overlap with a location of the inverted sequence in the target mitochondrial DNA sample.

* * * * *